United States Patent

McKenna et al.

Patent Number: 6,147,245
Date of Patent: Nov. 14, 2000

[54] PREPARATION AND USE OF α-KETO BISPHOSPHONATES

[75] Inventors: Charles E. McKenna, Pacific Palisades; Boris A. Kashcmirov, Venice, both of Calif.

[73] Assignee: University of Southern California University Park, Los Angles, Calif.

[21] Appl. No.: 09/352,236

[22] Filed: Jul. 13, 1999

Related U.S. Application Data

[60] Provisional application No. 60/092,568, Jul. 13, 1998.

[51] Int. Cl.$^7$ .................................................. C07F 9/40
[52] U.S. Cl. ........................................ 558/145; 558/161
[58] Field of Search ..................................... 558/145, 161

[56] References Cited

U.S. PATENT DOCUMENTS 4,208,401  6/1980  Baumann .

OTHER PUBLICATIONS

Kabachnik, M. I. et al. Reaction of trialkyl phosphites with phosgene Chemical Abstracts 53 (1959): 6988e.

Peng, Z–Y et al. Some phosphonic acid analogs as inhibitors of pyrophosphate–dependent phosphophofructinase, a novel target in Toxoplasma gondi. Biochem. Pharmacol. 49 (1995): 1055–13.

Kabachnik, M. I. et al. Reactions of chloroacetyl chloride, trichloroacetyl chloride and phosgene with trialkyl phosphites. Chemical Abstracts 51 (1957): No. 10366h.

Ismailov, V. M. et al. Some transformations of substituted vinylphosphonates. Azerb. Khim. Zh. 1980: 58–63; STN International, File CAPLUS, No. 1981: 497911.

Ebetino, F. H., Dansereau, S. M., Bisphosphonate on Bones; Bijvoet, O., Fleish, H. A. Canfield, R. E., Russell; G., Eds. Elsevier Science B. V. 1995, p. 139–153.

Zolotukhina, et al. Russian Chemical Reviews, 1993, 62, 647–659.

Mckenna, C. E.; Khare, A.; Ju, J.–Y.; Li, Z.–M.; Duncan, G.; Cheng, Y.–C,; Kilkuskie, R. Phosphorous Sukfur, 76: 139–142, 1993.

Breuer, E., The Chemistry of Organophosphorus Compounds; Hartley, F. R., John Wiley & Sons: New York, (1996) vol. 4 : 653–730, p. 685.

Regitz, M.; Adolph, H.–G. Liebigs Ann. Chem. 1969, 723, 47–60.

Tassignon, P.S.G., et al., (1995) Tetrahedron Lett., vol.43: p. 11 863–11 872.

McKenna, C. E.; Higa, M. T.; Cheung N. H.; McKenna, M.–C. Tetrahedron Letters (1977), 155–158.

McKenna, C. E.; Schmidthauser, J. J. Chem. Soc., Chem. Comm. (1979), 739.

*Primary Examiner*—Michael G. Ambrose
*Attorney, Agent, or Firm*—Fulbright & Jaworski L.L.P.

[57] ABSTRACT

A unique method for the synthesis of substantially pure α-keto bisphosphonate esters and the usage of these esters in reactions with C, N, O, or P nucleophiles for synthesis of α-functionalized bisphosphonates. The method starts with a reaction mixture formed of an α-diazo methanediphosphonate ester, including tert-butylchlorite, a polar aprotic organic solvent, and an effective amount of water. After synthesis is complete, a water trapping reagent may be added to remove any excess water. The present invention provides a versatile pathway to new α-substituted bisphosphonate derivatives and could be readily adapted to combinatorial drug discovery synthetic strategies. The α-keto bisphosphonate esters can be converted to the corresponding acids by acid hydrolysis or mild silyldealkylation.

25 Claims, No Drawings

PREPARATION AND USE OF α-KETO BISPHOSPHONATES

CROSS-REFERENCE WITH RELATED APPLICATIONS

This application claims the benefit of U.S. Provisional Application Ser. No. 60/092,568, filed Jul. 13, 1998.

BACKGROUND OF THE INVENTION

1. Field of the Invention

This invention relates generally to the field of phosphorus chemistry, and is particularly concerned with a novel method for the production of α-keto bisphosphonate esters (carbonylbisphosphonate esters) and the use of these esters in reactions with C, N, O, or P nucleophiles for synthesis of α-functionalized bisphosphonates.

2. Description of Related Art

There are several pathological conditions that involve irregularities in calcium and phosphate metabolism. Such conditions comprise bone related diseases including Paget's disease and osteoporosis, as well as osteolysis in bone metastases. Bone metastases present a major problem in many frequently occurring malignancies. Hypercalcemia, resulting from bone resorption, is a common and very important complication of malignancy, causing distressful symptoms, such as severe pain and spontaneous fractures, and may lead to a metabolic coma and death. Moreover, neoplastic cell-induced osteolysis may determine the localization and growth enhancement of bone tumors. (See, G. R. Mundy, Bone, 8, supp. 1, S9-5 16 (1987); and Calcium in Biological Systems, R. P. Rubin, G. B. Weiss, and J. W. Putney, Jr. eds. Plenum Press, N.Y. (1985). Other pathological conditions cause or result from deposition of calcium and phosphate anomalously in the body, such as rheumatoid arthritis and osteoarthritis.

In some common bone disorders, the balance between the process of resorption and formation remains normal, but the rate of bone turnover is much higher. Most cases of primary hyperparathyroidism, Paget's disease, and thyroxicosis are in this category. In other common diseases such as osteoporosis, there is an imbalance between resorption and formation. Whether increased resorption or impaired formation predominates, however, the consequence is the same, i.e., diminished total bone mass.

Natural pyrophosphates having the structure:

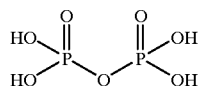

(1)

are known to be natural regulators of $Ca^{2+}$ metabolism at the cellular level. In recent years, many investigators have shown interest in the method of synthesis and biological activity of synthetic analogs of pyrophosphates, namely bisphosphonates and their derivatives. Bisphosphonic acids having the structure:

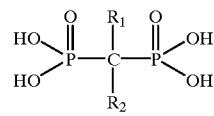

(2)

and their derivatives are pyrophosphate analogs in which the oxygen between the two phosphorus atoms is replaced by a carbon.

Bisphosphonates are a class of drugs that have been developed for use in various metabolic diseases of bone, the target being excessive bone resorption and inappropriate calcification and ossification. (M. D. Francis and R. R. Martodam, "The Role of Phosphonates in Living Systems" R. L. Hilderbrand, ed., CRC Press, Boca Raton, Fla., 1983, pp. 55–96; and H. Fleisch, Bone, 1987, 8, Supp. 1, S23–S28). A current theory attributes the biological activity of anti-resorptive bisphosphonates to two design components. One of these components is the so-called "bone-hook" functionality, associated with the bisphosphonate backbone, which is all of the molecule except the R group substituent in the following formula (3): $[(HO)_2P(O)CR(OH)P(O)(OH)_2]$. This bone-hook functionality is directly responsible for primary hydroxyapatite adsorption. The second design component is the bioactive moiety, R group, which is postulated to modulate the anti-resorptive potency of the drug within a given affinity class. See, Ebetino, F. H., Dansereau, S. M., Bisphosphonate on Bones; Bijvoet, O., Fleisch, H. A., Canfield, R. E., Russell, G., Eds. Elsevier Science B. V. 1995, p. 139–153. Numerous references disclose compositions containing polyphosphonates, in particular bisphosphonates, such as 1-hydroxyethylidenediphosphonic acid (HEDP) having the formula: $(HO)_2P(O)CCH_3(OH)P(O)(OH)_2$, where the R group in (3) is $CH_3$. See, U.S. Pat. Nos. 3,683,080 and 4,230,700 to Francis. See also, U.S. Pat. No. 4,868,164 to Ebetino, et al., which refers to heterocyclic bisphosphonates. HEDP is used in medicine under the name Etidronate (disodium salt of HEDP). HEDP is a useful complexing agent for alkaline earth, transition, and lanthanide metals. HEDP is also used to regulate calcium metabolism in the treatment of Paget's disease, to inhibit formation and growth of calcium oxalate stones in kidneys, and to reduce plaque when added to dental preparations. HEDP has also been suggested for use in treatment of diseases ranging from bone cancer to arthritis (See, Zolotukhina, et al., Russian Chemical Reviews, 1993, 62, 647–659). Numerous other references describe bisphosphonic acids useful for the treatment of osteoporosis and/or arthritis, and are herein incorporated by reference: U.S. Pat. No. 5,104,863 to Benedict, et al.; U.S. Pat. No. 4,267,108 to Blum, et al.; U.S. Pat. No. 4,754,993, to Bosies, et al.; U.S. Pat. No. 4,939,130 to Jaeggi, et al.; U.S. Pat. No. 4,971,958 to Bosies, et al.; DE 40 11 777 to Jaeggi; WO 90/12017 to Dunn, et al.; WP 91/10646 to Youssefyeh, et al.; AU-A-26738/88 to Jaeggi; AU-A-45467/89, assigned to Ciba-Geigy; and U.S. Pat. No. 4,208,401 to Bauman.

The elucidation and further development of structure-activity relationships in the bisphosphonate class of compounds has increasingly flourished during the past few years (See, Ebetino, F. H., et al., supra; and Zolotukhina, et al., supra.) Rational design of new medicinal agents based on bisphosphonates has progressed from simple α-alkyl and α-halo bisphosphonates, to bisphosphonates substituted with a range of heterocyclic and heteroatomic moieties.

Bisphosphonate chemistry has yielded an increasing variety of bone-active compounds, including potent anti-resorptive agents that have therapeutic potential in osteoporosis and other diseases of bone metabolism (See, Ebetino, F. H., et al., supra.) Variation in the P-C-P backbone has led to analogs of varied hydroxyapatite affinity, $Ca^{2+}$ chelation and anti-mineralization properties.

McKenna, et al., have reported the synthesis of crude carbonylbisphosphonate ester preparations by reaction of the corresponding α-diazo compounds with tert-butyl hypochlorite in formic acid, followed by a second step of pyrolytic distillation at reduced pressure. (See, McKenna, C. E.; Khare, A.; Ju, J. -Y.; Li, Z. -M.; Duncan, G.; Cheng, Y. -C.; Kilkuskie, R. *Phosphorus Sulfur,* 76:139–142, 1993). However, this method of synthesis suffers from serious defects: 1) The carbonylbisphosphonate esters are obtained in moderate to poor, erratic, yields, particularly due to the instability of the reaction mixture to prolonged heating; 2) An undesirable α-dichlorinated side product is usually formed, which resists attempts at removal; 3) Other impurities are often present, seen by NMR analysis. Furthermore, the vacuum pyrolysis in the second step is difficult to control and is difficult to scale up.

It has also been reported that reaction of carbanion nucleophiles such as Reformatsky reagents with α-keto monophosphonates (4) leads not to the desired α-hydroxy α-alkylated adduct (5) of the present invention, but instead to elimination of the phosphorus moiety forming a carbonyl product (6) and phosphite (7) (See, Breuer, E., *The Chemistry of Organophosphorus Compounds;* Hartley, F. R., Ed.; John Wiley & Sons: New York, (1996) Vol. 4: 653–730, p.685.)

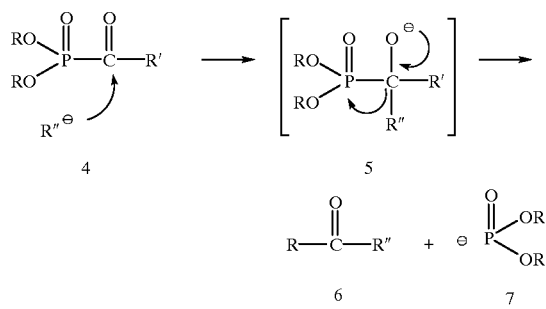

Hydrates of the impure carbonylbisphosphonate esters, prepared by the previous method of McKenna, et al., are readily formed by treatment with $H_2O$, however, the hydrates were not isolated. (See, McKenna, et al., supra.) Prior to the present invention, attempts to regenerate pure carbonylbisphosphonate esters, free of the α,α-dichloro contaminant and other impurities, have been unsuccessful. For example, in the previous method of McKenna, et al., the regeneration of carbonylbisphosphonate esters by evaporation (via heating and low pressure) of the aqueous phase, after extraction with an organic solvent, lead instead to formation of an unwanted product containing both phosphonate and phosphate groups.

It was previously reported that vicinal trioxo compounds can be obtained from corresponding α-diazo compounds through an "oxygen-halogen-insertion" reaction using t-BuOCl in formic acid, acetonitrile and other solvents (See, Regitz, M.; Adolph, H. -G. *Liebigs Ann. Chem.* 1969, 723, 47–60.) Regitz, et al., proposed that chloro-tertbutyloxydiacylmethanes are first formed, which decompose spontaneously into tertbutyl chloride and the trioxo product. As described above, an analogous approach led to the synthesis of crude carbonylbisphosphonate esters. (See, McKenna, et al., *Phosphorus Sulfur,* (1993), supra). The unsatisfactory nature of this method was initially ascribed to inadequate drying of the solvent, or non-optimal solvent. However, reactions carried out according to the previous procedure of McKenna, et al., between diazo MDP esters and t-BuOCl in different, very well-dried solvents, such as: acetonitrile; acetone; ethyl acetate; t-butanol; and $CCl_4$, still gave low yields of the desired products and was accompanied by the usual formation of unwanted side products, including α,α-dichlorinated bisphosphonate. (See, McKenna, et al., supra.) The intermediate product expected to be formed in the first step of this procedure, α-chloro-α-alkoxy methylenebisphosphonate, did not decompose spontaneously into the oxo product ($^{31}P$ NMR evidence), and thus required pyrolysis.

Regitz, et al., postulated that interaction between 2-diazo 1,3-oxo compounds and t-butylhypochlorite in alcohols involves intermediate formation of an α-diazonium α-chloro bisphosphonate species and a t-butoxide anion, followed by nucleophilic substitution of the $—N_2^+$ leaving group by an alcohol molecule ($S_N2$ or $S_N1$)(See, Regitz, et al., supra.) However, according to this mechanism, the first step, the formation of the α-diazonium α-chloro species and t-butoxide anion, requires release of t-butoxide, a very poor leaving group.

Generally, for efficient transfer of positive chlorine from alkylhypochlorite, an activated species, such as the protonated form of the alkoxide, is desirable as the leaving group. (See, Tassignon, P. S. G., et al., (1995) *Tetrahedron Lett.,* Vol. 43: p.11 863–11 872). Thus, t-butanol is a more reasonable leaving group in this reaction than t-butoxide. In formic acid the solvent provides a proton, but also the wrong nucleophile for carbonylbisphosphonate ester formation, which then must be removed in the inefficient pyrolysis step. The substitution taking place in the second step of this reaction, between the α-diazonium α-chloro bisphosphonate species and a nucleophile, therefore requires a nucleophile able to produce an intermediate that facilely leads to the desired carbonylbisphosphonate ester. Consequently, it appears there is a need for a better nucleophile for this reaction. Moreover, α-hydroxy bisphosphonates possess high affinity for hydroxyapatite and can be highly potent anti-resorptive agents, thus chemistry that generates a methylenebisphosphonate with an α-hydroxy function together with the addition of a R group is particularly desirable.

There continues to be a need for new bone-active agents. Design and synthesis of new bisphosphonates active against bone diseases would be greatly aided by preparative methodology facilitating introduction of the R moiety into the bisphosphonate structure. Such methodology, could also be employed for preparation of bisphosphonates that would be useful in treating many bone and other diseases, such as viral infections, or other health disorders that may be responsive to phosphonate drugs. (See, Zolotukhina, et al., supra.) Indeed, methodology facilitating introduction of a R group moiety into the bisphosphonate structure could be used to prepare any bisphosphonate possessing a particular utility or desirable property requiring introduction of a specific R group.

BRIEF SUMMARY OF THE INVENTION

The present invention solves the above-described problems by providing methods for readily converting α-diazo methylenebisphosphonate esters into substantially pure carbonylbisphosphonate esters in a simple and economical reaction, while suppressing the α,α dichloro by-product. In one embodiment of the invention the process for the preparation of carbonylbisphosphonate comprises: forming a reaction mixture of α-diazo methylenebisphosphonate ester, tert-butylhypochlorite, and a polar aprotic organic solvent; and adding an effective amount of water to the reaction mixture, whereby conversion of the α-diazo methylenebisphosphonate ester to the substantially pure carbonylbisphosphonate is substantially complete. One advantage of the present invention is that it does not require the additional step of heating for conversion to the bisphosphonate ester to be complete. Yet another advantage of the present invention is the resultant high yield of the substantially pure carbonylbisphosphonate esters. In another embodiment of the invention, the carbonylbisphosphonate ester so produced is utilized in ketone reactions with C, N, O, or P nucleophiles providing a versatile pathway for synthesis of α-functionalized bisphosphonates. One of many possible examples is the classical reductive amination of ketone which provides bisphosphonates having the structure:

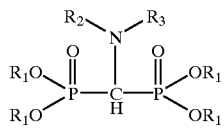

(8)

These α-functionalized bisphosphonates could be used in treatment or preventing diseases characterized by irregular calcium and phosphate metabolism, including osteoporosis and arthritis.

These and other features, aspects, and advantages of the present invention will become better understood with regard to the following detailed description and appended claims.

DETAILED DESCRIPTION OF THE INVENTION

The synthetically versatile ketone group in carbonylbisphosphonate esters having the structure:

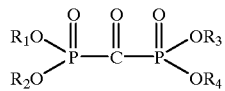

(9)

provides a convenient entry to a wide range of new α-substituted bisphosphonates via nucleophilic addition chemistry. $R_1$, $R_2$, $R_3$, and $R_4$ esterifying group, for example, when each are independently selected from alkyl (preferably having 1 to 24 carbon atoms), aryl (preferably having 6 to 30 carbon atoms), aralkyl (preferable having 7 to 24 carbon atoms) and hydrates thereof, which can serve as protecting groups and that are removable either chemically or metabolically.

One advantage of this approach in preparation of bone actives is that an α-hydroxy group may be generated with introduction of the R group moiety:

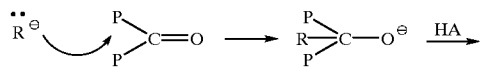
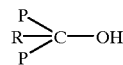

Herein we describe a new, mechanism-based approach to the synthesis of carbonylbisphosphonate esters and demonstrate exemplary reactions of these compounds with some C, N, O, and P-containing nucleophiles. This technology provides a versatile pathway to new α-substituted bisphosphonate derivatives and could be readily adapted to drug discovery synthetic strategies including combinatorial methods. Conversion of the product adducts, which are esters, to corresponding acids, could be effected in a variety of ways known to skilled practitioners, for example, from classical acid hydrolysis to much milder silyldealkylation with reagents such as bromotrimethylsilane. (See, McKenna, C. E.; Higa, M. T.; Cheung, N. H.; McKenna, M. -C. *Tetrahedron Letters* (1977), 155–158; and McKenna, C. E.; Schmidhauser, J. *J. Chem. Soc., Chem. Comm.* (1979), 739.)

The invention provides a new, rational understanding of the synthesis and reactive chemistry of α-keto bisphosphonate esters. The present invention solves a long standing problem in the synthesis of bisphosphonate derivatives namely, the preparation of pure carbonylbisphosphonate esters. Furthermore, it was surprisingly found that α-keto bisphosphonate esters, prepared in virtually pure form by the new method, readily reacted with a metalated carbanion reagents, e.g., Grignard, to give desired α-hydroxy α-alkylated bisphosphonates, rather than simply elimination products that might be expected by analogy with Breuer, E., supra.

The interaction of α-diazo methylenebisphosphonate esters with t-butylhypochlorite in ethyl acetate in the presence of 1–10 equivalents of water proceeded exothermically at room temperature, about 20° C., with evolution of $N_2$, and the reaction mixture was maintained at this temperature by cooling. The reaction formed the desired carbonylbisphosphonate ester in practically quantitative yield, greater than about 90%, within about 1 to 2 minutes after a typical induction period of about 2 to 5 minutes. The above kinetic behavior indicated an autocatalytic character of the reaction, wherein HCl, generated as a reaction product, accelerated the reaction by protonation of the t-butyloxy leaving group. However, an excess of hydrogen chloride product must be avoided, otherwise chlorination of the intermediate product of α-diazonium, α-chloro bisphosphonate may take place, which leads to dichlorinated side products. Thus, the concentration of water in the reaction mixture is crucial to the success of the synthesis. Although an excess of water, relative to the diazo substrate, is essential to eliminate formation of the dichlorinated side product, by providing $H_2O$ nucleophile to compete with Cl, too large an excess of water will convert the product carbonylbisphosphonate ester to its corresponding hydrate, which may lead to a decomposition pathway, see the scheme below. It is thus very important to remove excess water immediately after the reaction is completed, which occurs when the evolution of $N_2$ ceases. The removal of excess water can be conveniently effected by adding a suitable reagent that removes water, such as: $P_2O_5$, $SOCl_2$, and chlorotrimethylsilane (CTMS). The water trapping reagent CTMS was the preferable reagent for this purpose, as a liquid which reacts quickly with $H_2O$ forming hexamethyidisiloxane, an inert, volatile organic liquid, along with HCl. After removing the solvent, excess reagents, and by-products in vacuo, substantially pure carbonylbisphosphonate ester was obtained, and used directly in situ in further reactions.

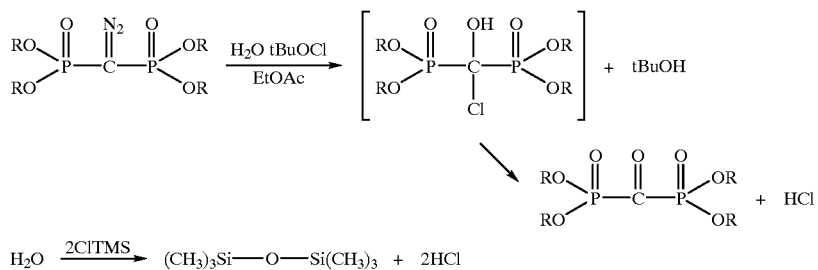

If the water-trapping reagent is omitted, the carbonylbisphosphonate product is converted to its hydrate (methyl and isopropyl carbonylbisphosphonate esters). The hydrates are easily isolated as colorless, crystalline compounds with well defined melting points. Treatment of these pure hydrates with $P_2O_5$ or magnesium perchlorate in organic solvents, such as: $CH_2Cl_2$, $CHCl_3$, ether, and acetonitrile conveniently regenerate the carbonylbisphosphonate esters.

Tetramethyl carbonylbisphosphonate hydrate readily dissolves in $H_2O$, where it decomposes to dimethyl hydrogen phosphonate, a process catalyzed by a base, such as: sodium acetate, and sodium bicarbonate. Other hydrates are also presumed to react according to the following scheme:

On heating, the carbonylbisphosphonate hydrates produce a product, whose NMR and Mass Spectrometry (MS) data are consistent with the products formed according to the following scheme.

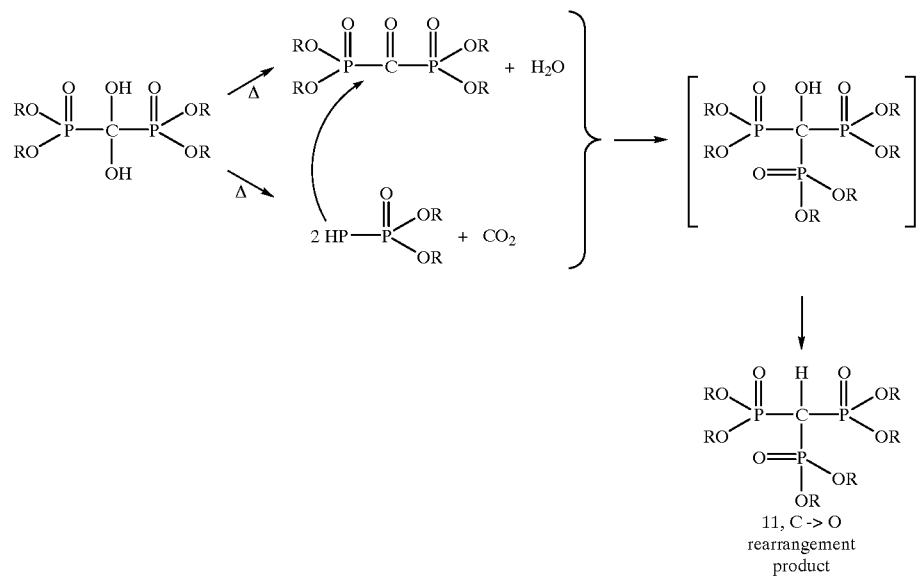

On heating, the hydrate 10 loses water to regenerate the carbonylbisphosphonate ester, and also decarboxylates to form dialkylphosphite. The phosphite adds to the carbonyl group of the carbonylbisphosphonate ester, giving an adduct which rearranges to the bisphosphonophosphate 11. To verify this scheme, the reaction between tetraisopropyl carbonylbisphosphonate and dimethyl phosphonate was investigated and is illustrated in the following scheme:

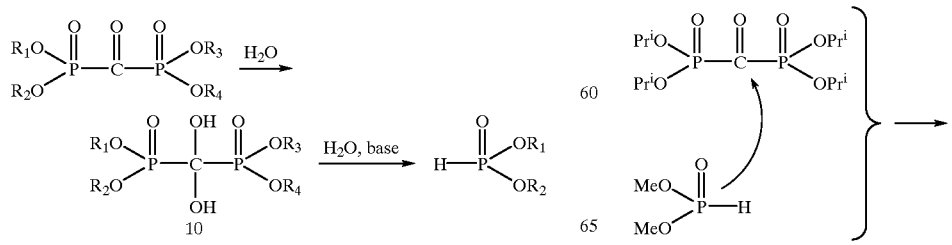

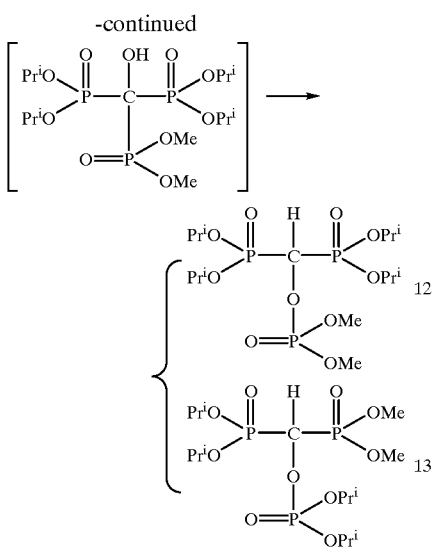

The formation of two products with the O-dimethoxyphosphoryl group (12) and O-diisopropoxyphosphoryl group (13), (12:13; ratio 1:0.75 by $^{31}$P NMR analysis), proved the instability of the intermediate α-hydroxy trisphosphonate, which has three phosphorus atoms connected to the α-carbon atom. Formation of the two products revealed that the migratory aptitude of the dimethoxyphosphoryl group was about 3 times higher than that of the diisopropoxyphosphoryl group in the subsequent rearrangement step. The formation of the compound, the O-diisopropoxyphosphoryl group (13), also demonstrated that nucleophilic phosphorus attacked at the carbon rather than the oxygen of the carbonyl group.

Referring now to the reaction chemistry of the ketones, according to literature cited above, dialkyl acylphosphonates are reported to react with metal carbanion reagents with the formation of carbonylbisphosphonate esters, as a consequence of the elimination of phosphite from the initial addition product. See, Breuer, E., supra. The carbonylbisphosphonate esters of the present invention serve as starting compounds for the synthesis of different α-alkylated, α-hydroxy methylenebisphosphonate derivatives by reaction with Grignard reagents. For example, the tetraisopropyl ester of HEDP was obtained from the reaction of tetraisopropyl carbonylbisphosphonate and methyl magnesium iodide. Other halogens can be substituted for iodine, such as chlorine or bromine. The reactions were carried out in mixed organic-ether solvents and yields of the desired products were from about 40 to 75%.

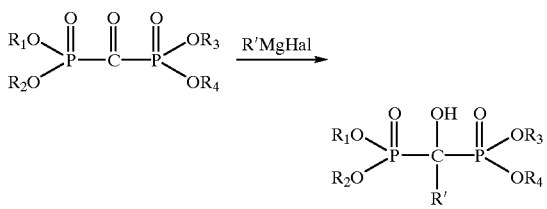

Wherein $R_1$, $R_2$, $R_3$, and $R_4$ are each independently selected from an alkyl and aryl group, which group may include a heterocyclic compound. As examples $R_1$, $R_2$, $R_3$, and $R_4$ are each independently isopropyl and ethyl; R' is alkyl or aryl group, which group may include a heterocyclic compound, as examples R' is methyl, phenyl, or arylalkyl.

It was previously reported that impure esters of carbonylbisphosphonate are converted to the corresponding aryl hydrazones by a standard reaction with aryl hydrazine. (See, McKenna, C. E., et al., supra.) The purer carbonylbisphosphonate esters made by the present invention described herein react smoothly with another nitrogen-containing nucleophile, $NH_2OMe$, giving oxime esters. For example, reaction of $iPr_4$ carbonylbisphosphonate gave the corresponding novel O-methyl oxime product in a 60% yield:

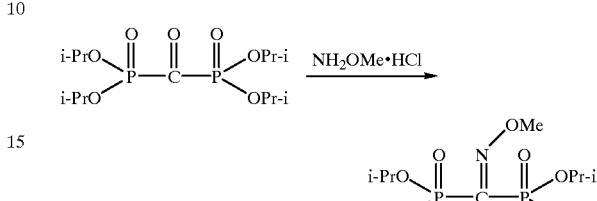

All reactions in these Examples were performed in scrupulously dried glassware under $N_2$. All solvents and reagents were of Analytical Reagent (AR) grade quality, purchased from Sigma-Aldrich, Inc. Nuclear Magnetic Resonance (NMR) spectra were recorded on a Bruker AM 360 spectrometer. $^1H$ and $^{13}C$ NMR chemical shifts (ppm) are referenced to tetramethylsilane. $^{31}P$ NMR chemical shifts (ppm) are referenced to external 85% $H_3PO_4$. Chemical shifts are reported in ppm. Melting points were recorded on a Thomas Hoover apparatus.

EXAMPLE 1

Synthesis of tetraisopropyl carbonylbisphosphonate

To a solution of tetraisopropyl α-diazo methylenebisphosphonate (74 mg, 0.2 mmol) in 4 ml ethyl acetate (0.14 M $H_2O$) cooled by an ice bath (about 10–15° C.) was added at least one equivalent, preferably 1.5 equivalents excess of t-butyl hypochlorite in 2 ml ethyl acetate (0.14 M $H_2O$). After about 2 to 5 minutes, $N_2$ rapidly evolved from the reaction mixture with a corresponding change in the reaction mixture color from colorless to yellow. 1 mM of chlorotrimethylsilane was then added to reaction mixture, and after about 5 minutes, 3 ml of the solvent was removed in vacuo. The resulting solution of carbonylbisphosphonate ester was used in different reactions without additional purification $^{31}P$ NMR (ethyl acetate): δ −4.9, the yield of product was approximately 95%.

EXAMPLE 2

Synthesis of tetramethyl carbonylbisphosphonate

By use of the same procedure as described in Example 1, tetramethyl α-diazo methylenebisphosphonate in 4 ml ethyl acetate (0.14 M $H_2O$) cooled by an ice bath (10–15° C.) was added a 1.5 excess of t-butyl hypochlorite in 2 ml ethyl acetate (0.14 M $H_2O$). After about 2 to 5 minutes, $N_2$ rapidly evolved with a corresponding change in the reaction mixture color to yellow. 1 mM of chlorotrimethylsilane was added to reaction mixture, and after 5 min, 3 ml of solvent was removed in vacuo. The resulting solution of carbonylbisphosphonate ester was used in different reactions without additional purification. $^{31}p$ NMR (ethyl acetate): δ −1.8, the resulting yield of product was approximately 93%.

EXAMPLE 3

Synthesis of tetraethyl carbonylbisphosphonate

By use of the same procedure as described in Example 1, tetraethyl α-diazo methylenebisphosphonate in 4 ml ethyl acetate (0.14 M $H_2O$) cooled by an ice bath (10–15° C.) was added a 1.5 excess of t-butyl hypochlorite in 2 ml ethyl acetate (0.14 M $H_2O$). After about 2 to 5 minutes, $N_2$ rapidly evolved with a corresponding change in the reaction mixture color to yellow. 1 mM of chlorotrimethylsilane was added to reaction mixture, and after 5 min, 3 ml of solvent was removed in vacuo. The resulting solution of methylenebisphosphonate was used in different reactions without additional purification. $^{31}$P NMR (ethyl acetate): δ –3.9, the resulting yield of product was approximately 94%.

EXAMPLE 4

Synthesis of hydrate of tetramethyl carbonylbisphosphonate

By use of the same procedure as described in Example 1, tetramethyl α-diazo methylenebisphosphonate in 4 ml ethyl acetate (0.14 M $H_2O$) cooled by an ice bath (10–15° C.) was added a 1.5 excess of t-butyl hypochlorite in 2 ml ethyl acetate (0.14 M $H_2O$). After about 2 to 5 minutes, $N_2$ rapidly evolved with a corresponding change in the reaction mixture color to yellow. However, the chlorotrimethylsilane was not added to the reaction mixture to remove the water in the last step. After 5 min, 3 ml of the solvent was removed in vacuo. Crystals of the hydrate were filtrated, and washed with dry ether. $^{31}$P NMR ($D_2O$): δ 16.9, the resulting yield of product was about 80%, and the m.p. 97–98° C.

EXAMPLE 5

Synthesis of hydrate of tetraisopropyl carbonylbisphosphonate

By use of the same procedure as described in Example 4, tetraisopropyl α-diazo methylenebisphosphonate in 4 ml ethyl acetate (0.14 M $H_2O$) cooled by an ice bath (10–15° C.) was added a 1.5 excess of t-butyl hypochlorite in 2 ml ethyl acetate (0.14 M $H_2O$). After about 2 to 5 minutes, $N_2$ rapidly evolved with a corresponding change in the reaction mixture color to yellow. Again, the chlorotrimethylsilane was not added to the reaction mixture to remove the water in the last step. About 2.5 equivalent volumes of pentane was added to the final solution until hydrate precipitation was induced. After 5 min, 3 ml of the solvent was removed in vacuo. Crystals of the hydrate were filtered, and washed with dry ether. $^{31}$P NMR ($D_2O$): δ 14.2, the resulting yield of product was about 20%; m.p. 49 to 51° C.

EXAMPLE 6

Synthesis of tetraisopropyl 1-hydroxy-ethylidenebisphophonate

Using the same reaction as described in Example 5, 2 mmol carbonylbisphosphonate ester was synthesized, but before the solvent was removed in vacuo, an equal volume of dry toluene was added 1:1 to the reaction mixture. ⅔ of the solvent was removed in vacuo, and a toluene solution of the carbonylbisphosphonate ester was added to a 5 ml ether solution of the Grignard reagent (5-fold excess) obtained from Mg and MeI at 5° C. After 10 min, the reaction mixture was diluted with 30 ml ether, washed with 20 ml cold (about 0 to 5° C.) 5% acetic acid and 20 ml water, and dried over $Na_2SO_4$. The solvent was removed in vacuo, and the compound purified by TLC. The yield was about 78%. The volume of eluent acetone to chloroform was 1:5. 31P NMR ($CDCl_3$): δ 19.3; $^{13}$C NMR ($CDCl_3$): δ 71.1, (t, $^2J_{pc}$=154 Hz. $^1$H NMR ($CDCl_3$): δ 1.6, t, $^3J_{PH}$=16 Hz.

EXAMPLE 7

Synthesis of tetraisopropyl hydroxy-phenylmethylenebisphosphonate

The same procedure as described in Example 6 was used, but the Grignard reagent was obtained from bromobenzene and Mg. The yield was about 38%. The compound was purified by TLC (benzene:ethyl acetate, 1:1). $^{31}$P NMR ($CDCl_3$): δ 15.7; $^1$H NMR ($CDCl_3$): δ 1.2–1.4 (m, 24H), 3.8 (broad s, 1H), δ 4.75–4.95 (m, 4H), 7.2–7.8 (m, 5H).

EXAMPLE 8

Synthesis of tetraethyl 1-hydroxy-2-phenylithyledenebisphosphonate

The same procedure as described in Example 6 was used, but the Grignard reagent was obtained from benzyl chloride and Mg. The yield was about 48%. The compound was purified by TLC (benzene:ethyl acetate, 1:1). $^{31}$P NMR ($CDCl_3$): δ 19.6. $^1$H NMR ($CDCl_3$): δ 3.3 (t, 2H) $^3J_{PH}$=13.4 Hz, 3.8 (broad s, 1H), 4.0 to 4.3 (m, 8H).

EXAMPLE 9

Synthesis of tetraisopropyl (O-methylhydroxyimino)methylenebisphosphonate

To 3 mmol of 0-methyl hydroxylamine hydrochloride (in 10 ml methanol) was added 3 mmol of NaOH. After addition, the reaction mixture was stirred for 1 hour. 2 mmol of tetraisopropyl carbonylbisphosphonate in 3 ml ethyl acetate, obtained as described in Example 1, was added, at room temperature, to the reaction mixture. After one day, the solution was filtered, and the solvent removed in vacuo. The compound was purified by column chromatography on silica gel, (acetone:$CH_2Cl_2$, 1:5). The yield of product was about 59%. 31P NMR ($CDCl_3$): dd δ 5.15, 1.95 $^2J_{PP}$=54.5 Hz. $^{13}$C NMR ($CDCl_3$): δ 23.5, 24.2, 64.0, 72.1, 72.5, dd 149.5, $^1J_{pc}$=196 Hz, $^1J_{pc}$=141 Hz. $^1$H NMR ($CDCl_3$): δ 1.2–1.4 (m, 24H), 4.18 (s, 3H), δ 4.75–4.95 (m, 4H).

The following references, discussed above, are all incorporated herein by reference: G. R. Mundy, Bone, 8, supp. 1, S9-5 16 (1987);, R. P. Rubin, G. B. Weiss, and J. W. Putney, Jr. Calcium in Biological Systems eds. Plenum Press, N.Y. (1985); M. D. Francis and R.R. Martodam, "The Role of Phosphonates in Living Systems" R. L. Hilderbrand, ed., CRC Press, Boca Raton, Fla., 1983, pp. 55–96; H. Fleisch, Bone, 1987, 8, Supp. 1, S23–S28; U.S. Pat. Nos. 3,683,080 and 4,230,700 to Francis; U.S. Pat. No. 4,868,164 to Ebetino, et al.; Zolotukhina, et al., *Russian Chemical Reviews,* 1993, 62, 647–659; U.S. Pat. No. 5,104,863 to Benedict, et al.; U.S. Pat. No. 4,267,108 to Blum, et al.; U.S. Pat. No. 4,754,993, to Bosies, et al.; U.S. Pat. No. 4,939,130 to Jaeggi, et al.; U.S. Pat. No. 4,971,958 to Bosies, et al.; DE 40 11 777 to Jaeggi; WO 90/12017 to Dunn, et al.; WP 91/10646 to Youssefyeh, et al.; AU-A-26738/88 to Jaeggi; AU-A-45467/89, assigned to Ciba-Geigy; and U.S. Pat. No. 4,208,401 to Bauman; Ebetino, F. H., Dansereau, S. M., *Bisphosphonate on Bones;* Bijvoet, O., Fleisch, H. A., Canfield, R. E., Russell, G., Eds. Elsevier Science B.V. 1995, p.139–153; McKenna, C. E.; Khare, A.; Ju, J. -Y.; Li, Z. -M.; Duncan, G.; Cheng, Y. -C.; Kilkuskie, R. *Phosphorus Sulfur,* 76:139–142, 1993; Breuer, E., *The Chemistry of Organophosphorus Compounds;* Hartley, F. R., Ed.; John Wiley & Sons: New York, 1996; 4: 653–730, p.685; Regitz, M.; Adolph, H. -G. *Liebigs Ann. Chem.* 1969, 723, 47–60; McKenna, C. E.; Higa, M. T.; Cheung, N. H.; McKenna, M.

-C. *Tetrahedron Lett.* (1977), 155–158; McKenna, C. E.; Schmidhauser, J. *J. Chem. Soc., Chem. Comm.* (1979), 739; and Tassignon, P. S. G., et al., (1995) *Tetrahedron Lett.*, Vol. 43: p.11 863–11 872.

In a further embodiment of the invention, the carbonylbisphosphonate ester so produced is utilized in ketone reactions with C, N, O, or P nucleophiles providing a versatile pathway for synthesis of α-functionalized bisphosphonates. One of many possible examples is the classical reductive amination of ketone which provides bisphosphonates having the structure:

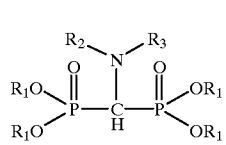

(8)

These α-functionalized bisphosphonates could be used in treatment or preventing diseases characterized by irregular calcium and phosphate metabolism, including osteoporosis and arthritis. The carbonylbisphosphonate esters may be reacted with metalated carbanions to form α-substituted α-hydroxy methylenebisphosphonate esters.

What is claimed is:

1. A process for the preparation of an α-keto bisphosphonate ester comprising:
   (a) forming a reaction mixture of an α-diazo methylenebisphosphonate ester, tert-butylhypochlorite, and a polar aprotic organic solvent; and
   (b) adding an effective amount of water to said reaction mixture, whereby conversion of the α-diazo methylenebisphosphonate ester to the substantially pure carbonylbisphosphonate ester is substantially complete.

2. The process of claim 1 further comprising adding a water trapping reagent, whereby to remove excess water after conversion to the α-keto bisphosphonate ester is substantially complete.

3. The process of claim 2 wherein said water trapping reagent is chlorotrimethylsilane.

4. The process of claim 1 wherein excess of said water is capable of forming an α-keto bisphosphonate ester hydrate with said α-keto bisphosphonate ester.

5. The process of claim 4 further comprising reacting said α-keto bisphosphonate ester hydrate with a reagent selected from the group consisting of $P_2O_5$ and magnesium perchlorate, in an organic solvent selected from the group consisting of $CH_2Cl_2$, $CHCl_3$, ether, and acetonitrile, whereby to regenerate the α-keto bisphosphonate ester.

6. The process of claim 1 further comprising maintaining said reaction mixture at a temperature from about 0° C. to about 30° C.

7. The process of claim 6 wherein said temperature is from about 20° C. to about 25° C.

8. The process of claim 1 wherein said polar aprotic organic solvent is ethyl acetate.

9. The process of claim 1 further comprising separating said α-keto bisphosphonate ester from said reaction mixture.

10. The process of claim 1 wherein the effective amount of water is about one to about ten equivalents of the water to said α-diazo methylenebisphosphonate ester.

11. The process of claim 1 further comprising reacting said substantially pure α-keto bisphosphonate ester with a carbon, oxygen, nitrogen, or phosphorus nucleophile.

12. The process of claim 11 wherein said carbon nucleophile is a metalated carbanion.

13. The process of claim 1 further comprising reacting said substantially pure α-keto bisphosphonate ester with a nitrogen-containing nucleophile, whereby to convert the α-keto bisphosphonate ester to an α-keto bisphosphonate imine or oxime ester.

14. The process of claim 1 wherein said α-keto bisphosphonate ester is a carbonylbisphosphonate ester.

15. The product prepared in accordance with the process of claim 1, comprising a substantially pure α-keto bisphosphonate ester represented by the general formula:

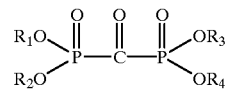

wherein $R_1$, $R_2$, $R_3$, and $R_4$ are each independently selected from alkyl and aryl.

16. A substantially pure tetramethyl carbonylbisphosphonate.

17. A substantially pure tetraethyl carbonylbisphosphonate.

18. A substantially pure tetraisopropyl carbonylbisphosphonate.

19. A process for the preparation of α-keto bisphosphonate ester comprising:
   (a) forming a reaction mixture comprised of α-diazo methylenebisphosphonate ester, tert-butylhypochlorite, a polar aprotic organic solvent; and an effective amount of water; and
   (b) maintaining the reaction mixture until a substantially pure α-keto bisphosphonate ester is obtained, whereby conversion of the α-diazo methylenebisphosphonate ester to the substantially pure α-keto bisphosphonate ester is complete.

20. The process of claim 19, further comprising separating the α-keto bisphosphonate ester from the reaction mixture.

21. The process of claim 19 wherein said α-keto bisphosphonate ester is a carbonylbisphosphonate ester.

22. The process of claim 12 wherein said α-keto bisphosphonate has the formula:

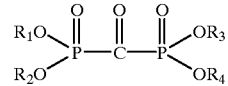

wherein $R_1$, $R_2$, $R_3$, and $R_4$ are each independently selected from an alkyl and aryl group, which group may include a heterocyclic compound.

23. A process comprising reacting the product of claim 1 with a phosphorus nucleophile, whereby to obtain a bisphosphonophosphate.

24. A process comprising reacting the compound of claim 15, whereby to form an α-amino-substituted bisphosphonate under reducing conditions.

25. A process comprising reacting the compound of claim 15, whereby to form an α-hydroxy-substituted bisphosphonate under reducing conditions.

* * * * *